United States Patent
Silberg

(10) Patent No.: US 10,137,290 B2
(45) Date of Patent: Nov. 27, 2018

(54) ULTRASONIC DISPERSION OF COMPOSITIONS IN TISSUE

(71) Applicant: Sonescence, Inc., Santa Rosa, CA (US)

(72) Inventor: Barry Neil Silberg, Santa Rosa, CA (US)

(73) Assignee: Sonescence, Inc., Santa Rosa, CA (US)

( * ) Notice: Subject to any disclaimer, the term of this patent is extended or adjusted under 35 U.S.C. 154(b) by 575 days.

(21) Appl. No.: 14/725,734

(22) Filed: May 29, 2015

(65) Prior Publication Data

US 2015/0297879 A1  Oct. 22, 2015

Related U.S. Application Data

(63) Continuation of application No. 13/374,221, filed on Dec. 15, 2011, now Pat. No. 9,446,227, which is a (Continued)

(51) Int. Cl.
*A61M 31/00* (2006.01)
*A61M 37/00* (2006.01)
(Continued)

(52) U.S. Cl.
CPC ....... *A61M 37/0092* (2013.01); *A61K 9/0009* (2013.01); *A61K 9/0019* (2013.01);
(Continued)

(58) Field of Classification Search
CPC .......................... A61M 37/0092; A61K 9/0009
(Continued)

(56) References Cited

U.S. PATENT DOCUMENTS

| | | |
|---|---|---|
| 3,630,198 A | 12/1971 | Henkin |
| 4,190,495 A | 2/1980 | Curtiss, III |
| (Continued) | | |

FOREIGN PATENT DOCUMENTS

| | | |
|---|---|---|
| RU | 2119769 C1 | 10/1998 |
| RU | 2175565 C2 | 10/2001 |
| (Continued) | | |

OTHER PUBLICATIONS

Barua et al,. "Convection-Enhanced Drug Delivery to the Brain: Therapeutic Potential and Neuropathological Considerations," Brain Pathology (2014) 24:117-127.
(Continued)

*Primary Examiner* — Edelmira Bosques
(74) *Attorney, Agent, or Firm* — Kilpatrick, Townsend & Stockton LLP

(57) ABSTRACT

Therapeutic agents, diagnostic agents and other compositions can be effectively delivered to target tissues using ultrasonic dispersion. For example, a therapeutic agent in solution may be injected subcutaneously in the vicinity of a target tissue in a patient. External ultrasound is used to disperse the therapeutic agent in the target tissue. The disclosed methods provide increased concentrations of therapeutic agents in tissue relative to traditional delivery methods, thereby improving therapeutic outcomes while reducing costs. In addition the methods can be used to deliver effective concentrations of therapeutic agents to tissues with limited blood supply.

16 Claims, 10 Drawing Sheets

Related U.S. Application Data continuation-in-part of application No. 13/205,097, filed on Aug. 8, 2011, now Pat. No. 8,747,384, which is a continuation of application No. 12/405,616, filed on Mar. 17, 2009.

(60) Provisional application No. 61/096,568, filed on Sep. 12, 2008.

(51) Int. Cl.
  *A61K 9/00*    (2006.01)
  *A61K 31/546*  (2006.01)
  *A61M 3/02*    (2006.01)
  *A61M 5/44*    (2006.01)
  *A61B 17/00*   (2006.01)

(52) U.S. Cl.
  CPC ......... *A61K 31/546* (2013.01); *A61M 3/0279* (2013.01); *A61M 5/445* (2013.01); *A61B 2017/00889* (2013.01); *A61M 2037/0007* (2013.01); *A61M 2205/3372* (2013.01)

(58) Field of Classification Search
  USPC ........................................................ 604/500
  See application file for complete search history.

(56) References Cited

U.S. PATENT DOCUMENTS

| | | | |
|---|---|---|---|
| 4,368,203 A | 1/1983 | Okamura et al. | |
| 4,982,730 A | 1/1991 | Lewis, Jr. | |
| 5,016,615 A | 5/1991 | Driller et al. | |
| 5,197,946 A | 3/1993 | Tachibana | |
| 5,399,723 A | 3/1995 | Iinuma et al. | |
| 5,559,108 A | 9/1996 | Kim et al. | |
| 5,578,572 A | 11/1996 | Horowitz et al. | |
| 5,580,575 A | 12/1996 | Unger et al. | |
| 5,884,631 A | 3/1999 | Silberg | |
| 5,928,138 A | 7/1999 | Knight et al. | |
| 5,980,512 A | 11/1999 | Silberg | |
| 5,980,549 A | 11/1999 | Chin | |
| 6,018,678 A | 1/2000 | Mitagotri et al. | |
| 6,030,374 A | 2/2000 | McDaniel | |
| 6,039,048 A | 3/2000 | Silberg | |
| 6,041,253 A | 3/2000 | Kost et al. | |
| 6,074,657 A | 6/2000 | Brown | |
| 6,228,082 B1 | 5/2001 | Baker et al. | |
| 6,277,137 B1 | 8/2001 | Chin | |
| 6,403,056 B1 | 6/2002 | Unger | |
| 6,428,491 B1 | 8/2002 | Weiss | |
| 6,464,680 B1 | 10/2002 | Brisken et al. | |
| 6,484,052 B1 | 11/2002 | Visuri | |
| 6,565,521 B1 | 5/2003 | Silberg | |
| 6,569,099 B1 | 5/2003 | Babaev | |
| 6,623,444 B2 | 9/2003 | Babaev | |
| 7,025,735 B2 | 4/2006 | Soring | |
| 7,083,572 B2 | 8/2006 | Unger et al. | |
| 7,326,235 B2 | 2/2008 | Edwards | |
| 7,981,442 B2 | 7/2011 | Hood et al. | |
| 8,050,752 B2 | 11/2011 | Babaev | |
| 8,747,384 B2 | 6/2014 | Silberg | |
| 2002/0099356 A1 | 7/2002 | Unger et al. | |
| 2003/0092667 A1 | 5/2003 | Tachibana et al. | |
| 2004/0162546 A1 | 8/2004 | Liang et al. | |
| 2004/0220551 A1 | 11/2004 | Flaherty et al. | |
| 2005/0054098 A1 | 3/2005 | Mistry et al. | |
| 2005/0187185 A1 | 8/2005 | Reinmuller et al. | |
| 2006/0222692 A1 | 10/2006 | Lane et al. | |
| 2006/0247601 A1 | 11/2006 | Ellin et al. | |
| 2007/0167619 A1 | 7/2007 | Love et al. | |
| 2007/0213688 A1* | 9/2007 | Klein .................... | A61M 5/158 604/523 |
| 2011/0301528 A1 | 12/2011 | Silberg | |
| 2012/0041309 A1 | 2/2012 | Coussios et al. | |
| 2012/0128776 A1 | 5/2012 | Chlon et al. | |
| 2012/0259222 A1 | 10/2012 | Coussios et al. | |
| 2012/0271169 A1 | 10/2012 | Coussios et al. | |
| 2013/0281916 A1 | 10/2013 | Wagstaffe et al. | |
| 2014/0276367 A1 | 9/2014 | Kersten et al. | |

FOREIGN PATENT DOCUMENTS

| | | |
|---|---|---|
| RU | 2218886 C2 | 12/2003 |
| RU | 2320381 C2 | 3/2008 |
| WO | 2015/059460 A1 | 4/2015 |
| WO | 2015/075442 A2 | 5/2015 |

OTHER PUBLICATIONS

Bratzler, Dale W., et al., "Use of Antimicrobial Prophylaxis for Major Surgery: Baseline Results From the National Surgical Infection Prevention Project", Arch Surg., (Feb. 2005), vol. 140, pp. 174-182.

Byl, Nancy, "The Use of Ultrasound as an Enhancer for Transcutaneous Drug Delivery: Phonophoresis", Pharmacology Series, Physical Therapy (Jun. 1995), vol. 75, No. 6, 15 pages.

Champoux, N. Et al., "Single-dose pharmacokinetics of ampicillin and tobramycin administered by hypodermoclysis in young and older healthy volunteers", Br J Clin Pharmacol, (1996), 42:325-331.

Dudley, Michael N., et al., "Comparative Penetration of Cefonicid and Cefazolin into the Atrial Appendage and Pericardial Fluid of Patients Undergoing Open-Heart Surgery", Antimicrobial Agents and Chemotherapy, (Sep. 1984), vol. 26, No. 3, p. 347-350.

Dyson, M. et al., "Stimulation of healing of varicose ulcers by ultrasound", Ultrasonics (Sep. 1976), pp. 232-236.

Forsberg et al., "Subharmonic imaging of contrast agents," *Ultrasonics,* (2000) 38:93-98.

Foulds, George, Joseph P. Stankewich, David C. Marshall, Mark M. OBrien, et al., Pharmacokinetics of Sulbactam in Humans, (May 1983), Antimicrobial Agents and Chemotherapy, vol. 25 No. 5, 692-699.

Frisoli, Jr., A. et al., "Subcutaneous Hydration By Hypodermoclysis: A Practical and Low Cost Treatment for Elderly Patients", Drugs & Aging, (Apr. 2000), 16 (4): 313-319.

Frohly et al., "Ultrasonic cavitation monitoring by acoustic noise power measurement," The Journal of the Acoustical Society of America, (2012) 108(5).

Hockham et al., "A Real-Time Controller for Sustaining Thermally Relevant Acoustic Cavitation During Ultrasound Therapy," IEEE Transactions on Ultrasonics, Ferroelectrics, and Frequency Control, (Dec. 2010) 57(12):2685-2694.

Hompland et al., "Interstitial Fluid Pressure and Associated Lymph Node Metastasis Revealed in Tumors by Dynamic Contrast-Enhanced MRI," *Cancer Research,* (2012) 72(19):4899-4908.

Kernodle, Douglas S. et al., "Association of Borderline Oxacillin-Susceptible Strains of *Staphylococcus aureus* with Surgical Wound Infections", Journal of Clinical Microbiology, (Jan. 1988), vol. 36, No. 1, pp. 219-222.

Lavery, Lawrence A., et al., "Validation of the Infectious Diseases Society of America's Diabetic Foot Infection Classification System", Clinical Infectious Diseases, (Jan. 17, 2007), 44:562-5.

Mangram, Alcicia J., et al., "Guideline for Prevention of Surgical Site Infection, 1999", Infection Control and Hospital Epidemiology, (Apr. 1999), vol. 20, No. 4, pp. 247-278.

Newman, M. K. et al., "Effects of Ultrasound Alonf and Combined with Hydrocortisone Injections by Needle or Hypospray", Presented as part of the Scientific pgrgram of the International Conference of Ultrasonics in Medicine, sponsored by the American Institute of Ultrasonics in Medicine, Los Angles, CA, (Sep. 6-7, 1957), pp. 206-209.

Ohge et al., "An Additional Dose of Cefazolin for Intraoperative Prophylaxis" Jpn J Surg (1999) 29:1233-1236.

Tranquart et al., "Clinical Use of Ultrasound Tissue Harmonic Imaging," Ultrasound in Med. & Biol., (1999) 25(6):889-894.

Tsukamoto, Akira, et al., "1-MHz ultrasound enhances internal diffusivity in agarose gels", Applied Acoustics (2013) 74:1117-1121.

(56) References Cited

OTHER PUBLICATIONS

Turos, Edward et al., "Penicillin-bound polyacrylate nanoparticles: Restoring the activity of β-lactam antibiotics against MRSA", Bioorganic & Medicinal Chemistry Letters, (Jun. 15, 2007) 17(2):3468-3472.
Wiggins, C.E., CL Nelson, R Clarke and CH Thompson, "Concentration of antibiotics in normal bone after intravenous injection", (1978), The Journal of Bone and Joint Surgery, 60, pp. 90-96.
As-filed U.S. Appl. No. 12/405,616, filed Mar. 17, 2009.
As-filed U.S. Appl. No. 13/205,097, filed Aug. 8, 2011.
As-filed U.S. Appl. No. 14/297,110, filed Jun. 5, 2014.
As-filed U.S. Appl. No. 14/725,694, filed May 29, 2015.
As-filed U.S. Appl. No. 14/738,606, filed Jun. 12, 2015.
As-filed U.S. Appl. No. 13/374,221, filed Dec. 15, 2011.

\* cited by examiner

| Organism | MIC/Cefazolin | Median MIC, μg/ml | Colony Count |
|---|---|---|---|
| MRSA 143 | 64 | 128 | 5.73E+05 |
|  | 128 |  | 4.18E+05 |
|  | 128 |  | 5.94E+05 |
| MRSA 144 | 128 | 64 | 5.12E+05 |
|  | 64 |  | 4.43E+05 |
|  | 64 |  | 5.15E+05 |
| MRSA 145 | 128 | 128 | 4.87E+05 |
|  | 128 |  | 7.50E+05 |
|  | 128 |  | 7.54E+05 |
| MRSA 146 | 64 | 64 | 5.79E+05 |
|  | 64 |  | 4.62E+05 |
|  | 128 |  | 5.68E+05 |
| MRSA 147 | 64 | 64 | 5.22E+05 |
|  | 64 |  | 3.71E+05 |
|  | 64 |  | 6.83E+05 |
| MRSA 148 | 256 | 256 | 3.45E+05 |
|  | 256 |  | 4.30E+05 |
|  | 128 |  | 4.37E+05 |
| MRSA 149 | 128 | 128 | 4.93E+05 |
|  | 128 |  | 6.97E+05 |
|  | 128 |  | 5.28E+05 |
| MRSA 150 | 512 | 512 | 4.67E+05 |
|  | 512 |  | 5.08E+05 |
|  | 512 |  | 4.92E+05 |
| MRSA 151 | 128 | 128 | 3.66E+05 |
|  | 128 |  | 4.91E+05 |
|  | 128 |  | 4.54E+05 |
| MRSA 152 | 4 | 4 | 4.03E+05 |
|  | 4 |  | 4.44E+05 |
|  | 8 |  | 5.55E+05 |
| STA 29213 | 0.5 |  | 3.02E+05 |
| MSSA | 1 |  | 5.63E+05 |
| MRSA56 (494) | 64 |  | 2.04E+05 |
|  | 128 |  | 5.84E+05 |
|  | 128 |  | 6.32E+05 |

Figure 4

| | | | |
|---|---|---|---|
| MRSA 116 | 512 | 256 | 7.40E+05 |
| | 256 | | 6.32E+05 |
| | 256 | | 5.24E+05 |
| MRSA 142 | 256 | 256 | 4.42E+05 |
| ATCC 33591 | 256 | | 5.26E+05 |
| MRSA | 256 | | 5.18E+05 |
| Mu 3 | 512 | 512 | 3.52E+05 |
| MRSA | 512 | | 4.20E+05 |
| hVISA | 512 | | 4.42E+05 |
| Mu 50 | 256 | 256 | 5.98E+05 |
| MRSA | 256 | | 2.68E+05 |
| VISA | 256 | | 2.70E+05 |
| STA 25923 | 0.5 | 0.5 | 5.72E+05 |
| MSSA | 0.5 | | 5.76E+05 |
| | 0.5 | | 5.82E+05 |
| STA 29213 | 0.5 | 0.5 | 4.04E+05 |
| MSSA | 0.5 | | 3.94E+05 |
| | 0.5 | | 5.88E+05 |

Figure 4 cont.

ULTRASONIC DISPERSION OF COMPOSITIONS IN TISSUE

CROSS-REFERENCE TO RELATED APPLICATIONS

The present application is a Continuation of U.S. Ser. No. 13/374,221 filed Dec. 15, 2011; which is a continuation-in-part of U.S. Ser. No. 13/205,097 filed Aug. 8, 2011 (now U.S. Pat. No. 8,747,384); which is a continuation of U.S. Ser. No. 12/405,616 filed Mar. 17, 2009; which claims priority to U.S. Provisional Appln No. 61/096,568 filed Sep. 12, 2008. The disclosures, all of which are incorporated herein by reference in their entirety for all purposes.

BACKGROUND OF THE INVENTION

Field of the Invention

The invention relates generally to delivery of compositions, such as therapeutic agents, to tissues.

Description of the Related Art

There are many variations in the routes of administration of therapeutic agents, including injection into a tissue such as muscle, intravenous injection and oral administration. When using current delivery methods, only a small percentage of the total dose of the therapeutic agent typically reaches the area where it is needed. This may be due to a variety of factors including, for example, dilution, lack of circulation in the target tissue and poor circulation in general. In some instances a therapeutically effective concentration of a pharmaceutical may be difficult or impossible to achieve in a target tissue. For example, it is often difficult to treat diabetic foot and leg ulcers with antibiotics due to the patient's poor circulation and this can lead to lower extremity amputation.

In many instances, a relatively high dose of therapeutic agent is required to provide enough of the therapeutic agent to a target region to achieve a desired therapeutic effect. Many therapeutic agents have undesirable side effects at high concentrations, and there is often a practical limit to the total dose that may be given to a patient. As a result, the concentration that can be achieved at the target site may be less than optimal. In addition, patients may require monitoring to ensure that the therapeutic agent is not causing more harm than necessary. Furthermore, therapeutic agents are often very expensive and thus the large doses required to achieve a therapeutic response increase the cost of treatment significantly.

SUMMARY OF THE INVENTION

Methods are provided for dispersing a composition of interest in a target tissue using ultrasound. In some embodiments the ultrasound is applied externally. The target tissue may be one with limited blood supply, and in some embodiments delivery of the composition in the tissue is independent of blood supply. A solution comprising the composition of interest is provided in the vicinity of the target tissue, such as by subcutaneous injection. Ultrasound is applied to disperse the composition in the target tissue. In some embodiments, the methods may be used to deliver a therapeutic agent to a tissue in a patient.

In one aspect, methods for treating a bacterial infection in a tissue in a patient are provided. A solution comprising an antibiotic may be delivered in the vicinity of an infected tissue. Ultrasound is applied to disperse the antibiotic in the infected tissue. The infected tissue may be one, for example, where there is limited blood supply. In some embodiments, a concentration of greater than 1000 micrograms/ml of antibiotic is initially achieved in the infected tissue. Ultrasound may be applied externally, for example at a power of about 1 to 3 watts/cm$^2$ in some embodiments. The ultrasound may also be applied at a frequency of about 1 to about 3.3 MHz.

In some embodiments the antibiotic is delivered subcutaneously or superficially, for example by injection. The volume of solution delivered may be, for example, about 100 to about 500 cc. In some embodiments the antibiotic may be Cefazolin, and the initial concentration of Cefazolin in the tissue may be about 2000 micrograms/ml or higher after applying the ultrasound.

In some embodiments, methods of treating a methicilin resistant *Staphylococcus aureus* (MRSA) infection in a tissue in a patient are provided. A tissue comprising an MRSA infection is identified and a solution comprising Cefazolin is provided, typically subcutaneously, adjacent to or into the infected tissue and ultrasound is used to disperse the Cefazolin in the infected tissue. Other antibiotics may be used in place of Cefazolin, such as Vancomycin. The ultrasound may be applied, for example, externally at a power of about 1 to about 3 watts/cm$^2$.

In some embodiments, about 1 to 3 grams of Cefazolin is provided, for example in about 100 to about 250 cc of solution. The solution may be provided, in some embodiments, by injection or infusion. The concentration of Cefazolin in the infected tissue immediately after providing the external ultrasound may be at least about 2000 micrograms/ml in some embodiments. An hour after providing the external ultrasound, the concentration of Cefazolin in the infected tissue may be at least about 1000 micrograms/ml. In some embodiments, the concentration of Cefazolin in the infected tissue is at least about 100 times the serum concentration immediately after providing the ultrasound.

In another aspect, methods of dispersing a therapeutic or diagnostic agent in a tissue are provided. The agent is delivered in the vicinity of the tissue, for example by injection or infusion of a solution comprising the agent. External ultrasound is then applied to disperse the agent in the tissue. The therapeutic agent may be, for example, a pharmaceutical. In some embodiments the therapeutic agent is an antibiotic, antiviral, or antifungal agent. In some embodiments the therapeutic agent is an anti-inflammatory agent. In some embodiments the therapeutic agent is an anti-cancer agent.

In a further aspect, methods of treating inflammation of a tissue in a patient are provided. An anti-inflammatory agent is provided in the vicinity of an inflamed tissue. For example, the agent may be injected or infused in a solution. The anti-inflammatory agent may be, for example, an NSAID or a steroid. External ultrasound is applied to disperse the anti-inflammatory agent in the inflamed tissue. In some embodiments the anti-inflammatory agent is injected or infused directly into the joint space of a patient, such as a patient suffering from arthritis.

In a still further aspect, methods of delivering a therapeutic agent to treat cancer are provided. The therapeutic agent, such as a chemotherapeutic or biologic, is delivered in the vicinity of a cancerous tissue, such as a tumor. External ultrasound is applied to disperse the anti-cancer agent in the cancerous tissue. In some embodiments the tissue is located in an area with limited or decreased blood supply. For example, a chemotherapeutic may be delivered to treat a chest wall recurrence of breast cancer.

BRIEF DESCRIPTION OF THE DRAWINGS

FIG. 4 is a table showing minimum inhibitory concentration (MIC) data for Cefazolin.

DETAILED DESCRIPTION

Figure 1:
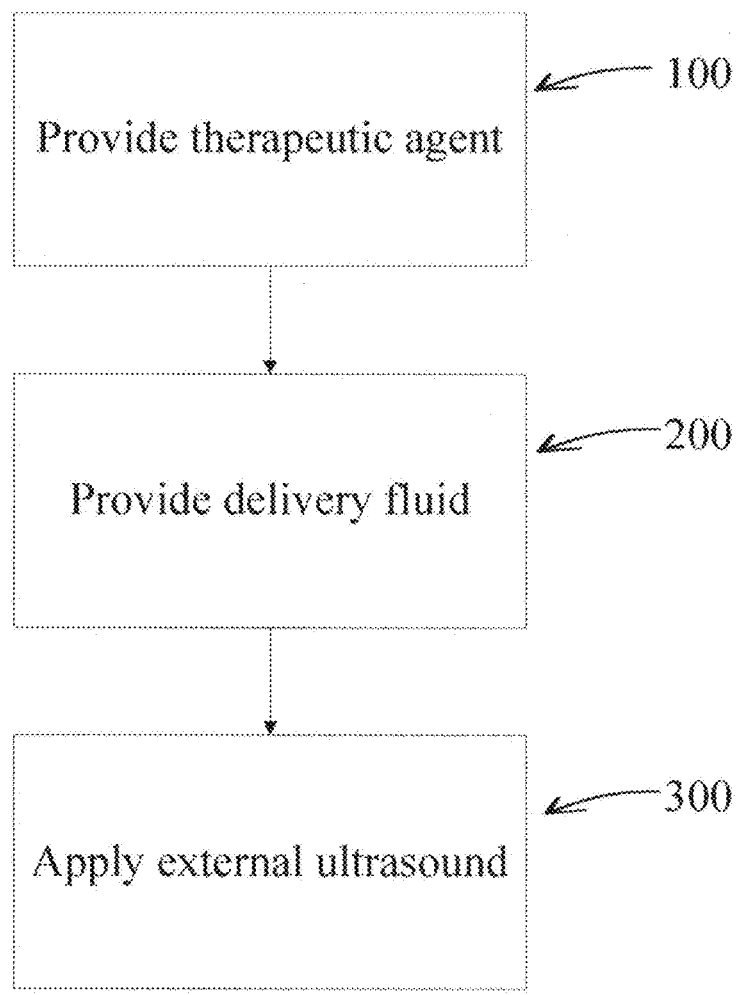
FIG. 1 is a flowchart illustrating one embodiment.

As discussed above, up until now it has been problematic to deliver compositions such as therapeutic agents to some tissues, particularly tissues in which there is limited blood supply. However, as disclosed herein, external ultrasound can now be used to deliver a composition to target tissues at effective concentrations that are much higher than can be achieved using traditional delivery methods. Moreover, as the delivery is not dependent on blood supply to the tissue, delivery of effective doses of therapeutic agents, such as antibiotics, to tissues with low or no blood supply is possible in some embodiments. In this way many diseases and disorders that were previously resistant to therapy can be treated. For example, and without limitation, MRSA infections, diabetic ulcers and other infections of soft tissue and bone can be treated using the disclosed methods. In addition, the techniques allow for the expanded use of some therapeutic agents that were previously not relevant in particular contexts because effective doses could not be delivered.

As an example, in some embodiments an antibiotic in solution is injected or infused in or near an infected tissue. External ultrasound is used to disperse the antibiotic through the infected tissue. The concentration of antibiotic achieved in the infected tissue can be at least an order of magnitude greater than the concentration that could be achieved by delivering antibiotics systemically or by local injection without ultrasound.

More generally, by applying ultrasound following administration of a composition in proximity to a tissue, the composition is dispersed in the tissue and reaches the site where activity is desired. In this way, a much higher concentration of the composition can be achieved at the desired location than can be achieved using traditional methods, such as systemic delivery. For example, in some embodiments an amount of an administered composition achieved per volume of tissue, when measured at the same time following delivery, may be at least 1000 times greater than can be achieved via intravenous injection or via oral, intramuscular or subcutaneous injection in the absence of ultrasound.

Although described primarily in terms of delivery of therapeutic agents, in some embodiments other types of compositions, such as diagnostic agents or prophylactic agents, may be delivered using the methods disclosed herein. This is discussed in more detail below.

Because the disclosed methods can achieve a higher local concentration of therapeutic agents in some target tissues, therapeutic outcomes for a wide variety of diseases and disorders can be greatly enhanced and the effectiveness of existing compounds can be improved. For example, based upon very low concentrations of Cefazolin that were attainable using the standard delivery methods (oral, intravenous, or intramuscular), methicillin resistant *Staphylococcus aureus* (MRSA) was perceived to be resistant to Cefazolin. Using the methods described herein, however, a dose of Cefazolin can be achieved in infected tissue that is effective at treating an MRSA infection. In some experiments, a tissue concentration of Cefazolin in deep subcutaneous adipose of the abdomen was shown to reach 2000 micrograms/ml in one hour and remained at 800 micrograms/ml two hours after subcutaneous injection of Cefazolin at a concentration of one gram in 250 ml of saline followed by dispersion using external high frequency and high power ultrasound for three minutes. This compared with tissue levels of 3-5 micrograms/ml of Cefazolin after one hour when the dose was given intravenously. In a study by David Nicolau at the Hartford Center for Anti-Infective Research and Development, the highest minimum inhibitory concentration (MIC) for Cefazolin against MRSA in vitro was 512 micrograms/ml (FIG. 4). Thus, while the concentration of Cefazolin achieved using intravenous delivery was well below this MIC, and thus would be ineffective therapeutically, the concentration obtained using the present methods far exceeded this MIC. Consistent with this finding, Cefazolin delivered to tissue using the disclosed methods has been effective in treating MRSA and other infections, as detailed in the Examples below.

In addition, in many instances less therapeutic agent is required and therapeutic outcomes can be achieved more rapidly, thus lowering costs. For example, in the treatment of MRSA infection, large systemic doses of an antibiotic such as Vancomycin have been routinely given. For example, routine treatment of a 70 kg adult with cellulitis might include a standard dose of 1 gram of intravenous Vancomycin every 12 hours for six weeks. By using the methods disclosed herein, much smaller local doses can be used, and dosing can be repeated less often, if at all. For example, as single dose of 1 gram of antibiotic may be effective in the treatment methods disclosed herein. In addition, less expensive therapeutics may be used effectively because an increased concentration can be achieved at the target site, such as the site of an infection.

Moreover, by avoiding systemic administration, side effects attributable to the systemic delivery of some therapeutic agents may be avoided. For example, side effects associated with prolonged, systemic delivery of antibiotics such as Vancomycin may be avoided.

Importantly, as mentioned above dispersal of the composition by the methods disclosed herein is not dependent on blood supply to the target tissue. Thus, tissues that do not have significant blood supply may be treated. Such tissues may inherently have a reduced blood supply, or the reduced blood may be due to other factors, such as decreased circulation in a patient. For example, in some embodiments the methods may be used to treat diabetic ulcers in the legs and/or feet of patients.

In some embodiments a patient is identified as being in need of delivery of a therapeutic agent (or other composition) to a target tissue, such as a tissue infected with a pathogen, a tissue at risk of infection (such as during surgery), an inflamed tissue or a cancerous tissue. A therapeutic agent is provided in the vicinity of the target tissue, typically in the form of a solution or suspension. For example, a solution or suspension containing the therapeutic agent may be injected under the skin. Ultrasound is subsequently applied to the area. The ultrasound is typically applied externally, for example through the skin, and disperses the therapeutic agent such that a therapeutically effective concentration is obtained in the target tissue. The ultrasound may be high power and/or high frequency ultrasound. In some embodiments, the Silberg Tissue Preparation System (TPS; Model ME 800 (9801427), available from Mettler Surgical (Anaheim, Calif.)) is used to apply the ultrasound.

A delivery fluid is used to facilitate dispersal of the composition in the target tissue by the ultrasound. Typically the delivery fluid comprises the therapeutic agent or other composition that is to be delivered. For example, the therapeutic agent may be in solution or suspension in a liquid that serves as the delivery fluid, such as water, saline or Ringer's solution. Thus, in some embodiments the therapeutic agent is dissolved or suspended in the delivery fluid and subsequently injected or infused adjacent to or directly into the target tissue.

In some embodiments, however, delivery fluid may be provided separately from the therapeutic agent. In some embodiments the therapeutic agent or other composition is provided in a fluid form, such as a liquid and additional delivery fluid is provided separately. However, in general a delivery fluid may be provided to or in the vicinity of the target tissue before, during and/or after the therapeutic agent or other composition has been provided, but prior to application of the ultrasound. The delivery fluid may absorb energy from the ultrasound, as well as facilitate dispersion of the therapeutic agent.

While the delivery fluid is typically a liquid, in some embodiments it may be a gel or other fluid.

As mentioned above, the tissue concentration of the composition obtained in the target tissue after ultrasonic dispersion can be significantly greater than the tissue concentration that can be obtained by traditional methods such as intravenous injection, oral delivery, or other methods of general systemic administration. Similarly, the tissue concentration of the composition obtained in the target tissue after ultrasonic dispersion can be significantly greater than the tissue concentration that can be obtained by direct local injection, or topical application. Concentration can be compared at the same time following administration by the different methods.

In some embodiments the tissue concentration achieved using the disclosed ultrasonic dispersal methods is many fold greater than by other methods. For example, in some embodiments, the maximum tissue concentration of the delivered therapeutic agent or other composition obtained in the target tissue is 0.5, 1, 2, 5, 10, 25, 50, 75, 100, 250, 500, 1000 or more times greater than the maximum tissue concentration that could be achieved in the target tissue by systemic administration of the therapeutic agent, such as by intravenous injection or oral delivery. In some embodiments, the maximum tissue concentration of the delivered therapeutic agent or other composition obtained in the target tissue is 0.5, 1, 2, 5, 10, 25, 50, 75, 100, 250, 500, 1000 or more times greater than the tissue concentration that could be achieved in the target tissue by direct local administration of the therapeutic agent without the application or ultrasound. In some embodiments the tissue concentration of a therapeutic agent or other composition achieved at a given time following ultrasonic dispersal is 0.5, 1, 2, 5, 10, 25, 50, 75, 100, 250, 500, 1000 or more times greater than the tissue concentration achieved at the same time following systemic or local delivery of the therapeutic agent or composition.

In some embodiments, as illustrated schematically in FIG. 1, a method of administering a therapeutic agent to a target tissue begins by providing a therapeutic agent 100 in, or in the vicinity of the target tissue. The therapeutic agent may be provided, for example, in solution or suspended in a liquid. The therapeutic agent may be provided by subcutaneous injection or infusion, for example in an area overlying the target tissue. In some embodiments the therapeutic agent is provided by subcutaneous injection or infusion in or near the target tissue. In other embodiments the therapeutic agent may be provided by superficial injection or infusion in, near or over the target tissue.

A delivery fluid is provided 200. The delivery fluid may be provided with the therapeutic agent and/or separately from the therapeutic agent. However, typically the therapeutic agent is dissolved or suspended in the delivery fluid. As discussed below, the amount of delivery fluid may be determined based on the particular circumstances. Factors may include the size of the tissue to be treated, the type and location of the tissue, the nature of the therapeutic agent and the power of the ultrasound to be delivered.

External ultrasound is subsequently applied 300 to disperse the therapeutic agent such that an effective concentration is achieved at the target tissue. The ultrasound may be high frequency and/or high power, as discussed in more detail below.

External high frequency ultrasound may be broadcast transcutaneously to disperse the therapeutic agent into the target tissue. The delivery fluid may add extra hydration to the treated area, thus reducing or preventing dehydration during the process, and may reduce the heat generated by the ultrasound, thus reducing or preventing tissue damage.

The methods disclosed herein can be used in any application where a therapeutic agent or other composition is to be delivered to a tissue. For example, the methods can be used to deliver antibiotics to treat and/or prevent tissue infections. In some embodiments the methods can be used to deliver therapeutic agents to tissue treat inflammation, such as arthritis. For example, a therapeutic agent such as a steroid or other anti-inflammatory may be delivered to a joint capsule to treat or prevent arthritis. In some embodiments, the methods may be used to treat cancer. For example, one or more therapeutic agents may be delivered to a cancerous tissue, such as a tumor. As an example, a therapeutic agent may be delivered to a chest wall recurrence of breast cancer in a radiated field with limited blood supply. In some embodiments the composition may be a diagnostic agent. For example, the diagnostic agent may be an antibody that recognizes an antigen associated with a disease or disorder. In some embodiments the tissue in which the therapeutic agent, or other composition to be delivered is one in which it is difficult to achieve a desired concentration of the composition by systemic delivery methods or by local injection in the absence of ultrasonic dispersal.

The target tissue is generally a tissue in which an effective concentration of a composition, such as a therapeutic agent, is desired. In some embodiments, the target tissue may comprise a specified volume of tissue. In some embodiments, the target tissue may include one or more types of tissue. In some embodiments, the target tissue may be one in which a therapeutic is not easily delivered systemically or by local delivery in the absence of ultrasound. For example, in some embodiments, the target tissue may be a tissue with little or no blood supply.

The disclosed methods can be used to deliver compositions to many different types of target tissues. For example, target tissue can comprise soft tissue, connective tissue, muscle tissue, nervous tissue and/or epithelial tissue. In some embodiments, target tissues may comprise, but are not limited to, one or more of skin, bone, tendons, muscles, joints, vessels, subcutaneous tissues such as subcutaneous fat, and internal organs. In some embodiments a target tissue is not an organ of the abdominal cavity or tissue within the spinal column or cranium.

The skilled practitioner can adjust the dose of the compositions, such as a therapeutic agent, that is provided, as well as the volume of the delivery fluid, to achieve an effective concentration in the target tissue. For example, if a larger tissue is to be treated a larger volume of delivery fluid and/or larger amount of therapeutic agent may be used. In some embodiments the dose is larger than the minimal dose necessary to achieve a desired outcome. However, the dose is preferably low enough that undesirable side effects are kept at or below an acceptable level.

An effective concentration is a concentration at which the activity for which the composition has been administered may be measured or observed in some way. Thus, for a therapeutic agent an effective concentration is one in which activity of the therapeutic agent can be observed in the target tissue. Observation may be direct observation or indirect observation. For example, the effect of the therapeutic agent may be observed by observing changes in the target tissue directly, such as healing or reduction of inflammation. In other embodiments the effect of the therapeutic may be measured indirectly, such as by changes in analytes associated with the target tissue, or by observations of a patient's health. The activity may, but does not have to, result in a measurable change in a clinical indication related to a disease or disorder in the target tissue.

Therapeutic Agents

The therapeutic agent is not limited in any way and includes any material that can be used to treat or prevent a disease or disorder, reduce one or more symptoms associated with a disease or disorder, or otherwise aid in treatment or prevention of a disease or disorder. In some embodiments a therapeutic agent is used to treat a disease or disorder that has been identified in a tissue in a patient. In some embodiments, the therapeutic agent is used to prevent or help prevent the onset or spread of a disease or disorder, such as the development of an infection following surgery.

Therapeutic agents that may be used, include, for example and without limitation, small molecules, organic compounds, proteins, peptides, antibodies, antibody fragments, vaccines, etc. . . . . In some embodiments the therapeutic agent may comprise two or more biologically active materials, such as two or more different pharmaceuticals. In some embodiments the therapeutic agent may be an antibiotic. In some embodiments the therapeutic may be an antiviral. In some embodiments the therapeutic may be an anti-inflammatory. In some embodiments the therapeutic may be an anti-fungal. In some embodiments the therapeutic may be an anti-cancer composition. In some embodiments the therapeutic may be a chemotherapeutic. Other types of therapeutic agents that can be delivered using the disclosed methods will be apparent to the skilled artisan.

In some embodiments, the therapeutic agent comprises an excipient. Excipients may include but are not limited to antiadherents, binders, coatings, disintegrants, fillers and diluents, lubricants, glidants, preservatives, and sorbents. In some embodiments, the therapeutic agent may comprise one or more active ingredients and one or more excipients.

The therapeutic agent is provided in appropriate form for delivery to a desired target tissue. In some embodiments the therapeutic agent is in solution or in a suspension. In some embodiments the therapeutic agent is provided in injectable form. In some embodiments the therapeutic agent is infusible.

In some embodiments the therapeutic agent may be packaged in a carrier. For example, the therapeutic agent may be packaged in liposomes or vesicles.

The therapeutic agent is delivered to the patient in the vicinity of the target tissue where the activity of the therapeutic agent is desired. For example, the therapeutic agent may be delivered in or near a tissue with a bacterial infection. In some embodiments the therapeutic agent is delivered by subcutaneous or superficial injection or infusion over, adjacent to, or directly in the target tissue.

In some embodiments the therapeutic agent is provided at the specific location where the therapeutic activity is desired. In other embodiments the therapeutic agent is provided at a distance from the location where the therapeutic agent is desired. However, the distance is such that upon application of the ultrasound, the agent disperses to the area where the therapeutic activity is desired at an effective concentration. In some embodiments, the vicinity of the target tissue where the therapeutic is delivered may be an area in, near, or surrounding the target tissue.

The skilled practitioner can determine the optimal site of delivery of the therapeutic agent based on the particular circumstances, for example the type of therapeutic agent, the type of target tissue and type of disease or disorder that is being addressed.

The therapeutic agent may be provided by any method known in the art. In some embodiments the therapeutic agent may be provided by injection or infusion. In some embodiments, the therapeutic agent is provided transdermally. The specific type of provision may be selected by the skilled artisan in view of the particular circumstances.

In some embodiments, the therapeutic agent is provided superficially to the target tissue, such as by injection or infusion. For example, in some embodiments, the therapeutic agent is provided under the skin close to the surface.

In some embodiments, the therapeutic agent may be provided subcutaneously, by subcutaneous injection or subcutaneous infusion.

The amount of the therapeutic agent provided may be determined based on the particular circumstances, including the nature of the therapeutic agent itself, distance from the site of administration to the target tissue, the type of tissue, the power and frequency of the ultrasound that can be applied, and the desired and/or effective concentration to be achieved in the target tissue. In addition, the amount of therapeutic agent may be adjusted in subsequent delivery depending on the therapeutic outcome achieved and/or the concentration achieved in the target tissue. In some embodiments the amount of therapeutic agent provided is such that a larger concentration than a minimal effective concentration is achieved in the target tissue.

Delivery Fluid

A delivery fluid is provided prior to administering the ultrasonic energy to disperse the therapeutic agent or other composition. Typically the delivery fluid is a liquid comprising the composition that is to be delivered to the target tissue. For example the delivery fluid may be a liquid, such as an isotonic saline solution, in which a therapeutic agent is dissolved. In some embodiments, however, the delivery fluid is administered separately from the therapeutic agent or other composition.

The delivery fluid may serve one or more of a variety of functions. For example, the fluid may aid in dispersal of the therapeutic agent in the tissue, attenuate the ultrasonic energy to reduce heating and protect the tissue, hydrate the tissue, and/or act as a carrier for the therapeutic agent, such as by dissolving the therapeutic agent or forming a suspension with the therapeutic agent. The fluid may be warmed to body temperature and is delivered to an area near the target tissue and/or directly to the target tissue itself. The fluid may be a liquid such as water, saline solution or isotonic solution. In other embodiments the fluid may be a gel or other fluid.

The delivery fluid may be provided before, during and/or after the administration of the therapeutic agent but prior to application of ultrasonic energy. However, in some embodiments additional delivery fluid can be provided after the ultrasound has commenced. In some embodiments fluid can be infused continuously during application of the ultrasound.

The delivery fluid may be provided by any known method, such as by injection or infusion. The amount of fluid may vary depending upon a variety of factors, such as the area to be infused, the type and location of the target tissue, the specific disease or disorder and the power/frequency of the ultrasound to be used. In some embodiments the amount of delivery fluid may be from about 1 to about 1000 cc or more, from about 1 to about 500 cc, from about 1 to about 250 cc, about 100 to about 250 cc, about 100 cc or about 250 cc. In some embodiments a therapeutic agent or other composition is delivered in about 100 cc of delivery fluid. In some embodiments a therapeutic agent or other composition is delivered in about 250 cc of delivery fluid.

In some embodiments, the delivery fluid is provided with the therapeutic agent. For example, the therapeutic agent may be dissolved in the fluid, or suspended in the fluid. In other embodiments, the fluid is provided simultaneously, but separately from the therapeutic agent. In some embodiments, the fluid is provided to the patient first and the therapeutic agent is provided after the fluid.

In some particular embodiments, 1 g of antibiotic, such as Cefazolin, may be dissolved in 100 cc of liquid and the solution delivered by injection or infusion. In some embodiments, 3 g of antibiotic, such as Cefazolin, may be delivered by injection or infusion of 250 cc of solution.

In some embodiments the delivery fluid comprises one or more ingredients different from the therapeutic agent. In some embodiments the delivery solution comprises one or more salts. In some embodiments, the delivery fluid may comprise one or more ingredients that aid in reducing heating due to the application of ultrasonic energy, or that protect cells from the ultrasonic energy. The delivery fluid may comprise a buffer or other composition, such as a composition that aids in the activity of the therapeutic agent. In some embodiments the fluid comprises one or more compounds that stabilize the therapeutic agent. In some embodiments the fluid may comprise one or more biologically active materials that are different from the therapeutic agent to be delivered to the target tissue.

Ultrasound

After provision of the therapeutic agent and delivery fluid, ultrasound is applied to the area to diffuse the therapeutic agent in the target tissue. In some embodiments the ultrasound is high power and/or high-frequency ultrasound. In some embodiments the ultrasound is applied externally, such as transdermally. It will be appreciated that the therapeutic agent preferably attains at least an adequate tissue concentration in the target tissue to achieve the desired effect. In some embodiments, a desired concentration to be obtained may be determined based on the type or degree of disease or disorder, such as infection or injury.

Without wishing to be held to a particular theory, the application of the ultrasonic energy is believed to cause cavitation and microstreaming, i.e., the movement of the fluid in a linear direction away from the ultrasonic energy source. In addition, if the therapeutic agent is packaged, such as in liposomes or vesicles, the ultrasonic energy may burst or otherwise open the packaging, releasing the therapeutic agent and dispersing it in the target tissue.

The frequency of ultrasound delivered to the target tissue can be selected as desired for a given situation. For example, the ultrasound may be delivered at a frequency of about 0.5 to about 10 MHz, about 1 to about 5 MHz or about 1 to about 3.3 MHz. In some embodiments, the ultrasonic field is introduced into the tissue through the skin at a frequency of about 1 MHz. In some embodiments, the ultrasonic field is introduced into the tissue through the skin at a frequency of about 3 MHz.

In some embodiments, high power ultrasound is used to disperse the therapeutic agent to the target tissue. For example, the ultrasound may be applied at a power of 0.1 to 25 watts/cm$^2$, or about 1 to 10 watts/cm$^2$. However, in some embodiments the ultrasound is applied at a power of about 1 to about 3 watts/cm$^2$. In some embodiments, the ultrasound is applied at a power of about 3 watts/cm$^2$. The power can be controlled to achieve an effective concentration in a target tissue, taking into account such factors as tissue density, distance of the target tissue from the site of administration of the therapeutic agent and the size of the target tissue. The power is preferably maintained low enough to avoid tissue injury, such as burns, while achieving adequate dispersal.

The power may be controlled such that no significant tissue damage is caused by the delivery of the ultrasound. However, in some embodiments, some tissue damage may be acceptable to achieve a desired concentration of therapeutic agent in a particular target tissue. In some embodiments the temperature of the site is monitored and the ultrasound is reduced, modified, or discontinued if excess heat buildup is detected. In some embodiments, additional fluid may be provided during delivery of the ultrasound to reduce the heat build up.

The ultrasound is typically applied externally through the skin over or adjacent to the treatment region, such that the ultrasonic waves disperse the therapeutic or other composition in the target tissue.

Any suitable ultrasound device can be used. A suitable ultrasound device is capable of delivering the power density and frequencies that cause dispersion of the therapeutic agent throughout the target tissue. The ultrasound device can be designed to deliver energy over a broad area or in a focused region. In some embodiments, the ultrasound device is a Silberg Tissue Preparation System Model ME 800 (9801427), available from Mettler Surgical (Anaheim, Calif.).

In some embodiments, the ultrasonic instrument comprises a handle coupled to a power source, and an ultrasonic transducer head is used to apply ultrasonic energy though the skin of the patient to the volume of tissue which is to receive the therapeutic agent. A transmitting gel is usually applied to the skin to provide coupling between the ultrasonic transducer head and the patient's skin for the efficient transmission of the ultrasonic waves. The physician typically holds the instrument by the handle and applies the transducer head to the patient's skin, moving the transducer generally over the intended target tissue region but most generally throughout the area of skin corresponding to the volume of tissue beneath the skin to be treated.

The duration which the ultrasound is delivered to the target tissue can be selected as desired for a given application. The ultrasound is typically continued for a time sufficient to disperse the therapeutic agent throughout the target tissue. In some embodiments the ultrasound is continued until at least an effective concentration of therapeutic agent in the target tissue is achieved. In some embodiments, the ultrasound is applied for one to ten minutes or more. In some embodiments, the ultrasound is applied for about three minutes. In other embodiments the ultrasound may be continued for less than one minute. In some embodiments the ultrasound is provided for about 1 s, 10 s, 15 s, 30 s, 45 s, 60 s, 90 s, 2 minutes, 3 minutes, 4 minutes or 5 minutes. In some embodiments the ultrasound is provided continuously. In other embodiments the ultrasound may interrupted one or more times during provision.

In some particular embodiments, the ultrasonic field is introduced into the target tissue through the skin at a frequency of about 1 MHz and a power density of about 3 watts/cm$^2$ for a sufficient time for the tissues to become warm and soft, generally about 2 to 5 minutes. In some embodiments an ultrasonic frequency of about 0.5 to 5 MHz is used with a power density ranging from about 2.5 to 4 watts/cm$^2$.

Alternative energy sources may be used to disperse the composition in the target tissue, such as acoustic waves that heat the tissue with pressure from the sound waves, and electromagnetic radiation, such as e.g. light, collimated light, laser or radio frequency energy that is used in a manner that minimizes cell damage while it disperses the drug and fluid.

Following administration of the ultrasonic energy, the concentration of therapeutic agent or other composition may be measured in the target tissue. Based on the measured concentration, the process can be adjusted to achieve a higher or lower concentration in subsequent applications of the process. For example, one or more of the dosage of therapeutic agent, amount of delivery fluid, ultrasound power and time of ultrasound application can be adjusted to achieve a desired concentration of therapeutic agent in the target tissue.

It is also possible to measure the therapeutic effect of the treatment. For example, clinical indications of the effectiveness of the treatment may be assessed. Based on the clinical indications, the process can be adjusted to achieve a higher or lower concentration in subsequent applications of the process, either in that patient or in other patients. For example, one or more of the dosage of therapeutic agent, amount of delivery fluid, ultrasound power, ultrasound frequency and time of ultrasound application can be adjusted to achieve a desired clinical outcome.

The process of providing a therapeutic agent, providing a delivery fluid and using ultrasound to disperse the therapeutic agent to the target tissue (ultrasonic dispersion of the therapeutic) may be repeated one or more times, at any desired interval, to achieve the desired clinical outcome. For example, the ultrasonic dispersion process can be repeated hourly, daily, weekly, monthly, or any combination thereof.

As mentioned above, in some embodiments a far higher concentration of therapeutic agent will be achieved at the target tissue than could be attained by traditional delivery methods. In addition, the patient may be given only a small fraction of the total dose traditionally used for a given therapeutic composition. For example, high concentrations of antibiotics that are toxic, such as Vancomycin, can be provided to a site of infection using a small fraction of the total intravenous dose that would traditionally be given or that would be required to achieve the same concentration in an infected tissue. In some embodiments, a therapeutic agent can be given in a concentration that if given systemically would not be effective.

In some embodiments the maximum concentration of the therapeutic agent in the target tissue following ultrasonic dispersion is 0.5, 1, 2, 5, 10, 25, 50, 75, 100, 250, 500, 1000 or more times greater than the maximum concentration of the therapeutic agent in the target tissue that is achieved by systemic administration (e.g. oral or intravenous) or direct administration (e.g. local injection or topical) without the application of ultrasound. Similarly, in some embodiments the concentration of the therapeutic agent in the target tissue at a given time following ultrasonic dispersal is 0.5, 1, 2, 5, 10, 25, 50, 75, 100, 250, 500, 1000 or more times greater than the maximum concentration of the therapeutic agent in the target tissue at that time following systemic administration (e.g. oral or intravenous) or direct administration (e.g. local injection or topical) without the application of ultrasound.

Because the therapeutic agent is delivered locally using the ultrasonic dispersion methods disclosed herein, the systemic concentration of the therapeutic agent can be kept low. In some embodiments, the dispersed therapeutic agent or other composition may be present in the target tissue at high concentrations, but present at low systemic concentrations. In some embodiments, immediately following ultrasonic dispersion in a target tissue the concentration or a therapeutic agent or other composition in the target tissue is about 10, 25, 50, 100, 200, 400, 500, 1000 or more times the serum concentration. In some embodiments, the tissue concentration in the target tissue is about 1, 10, 20, 40, 50, 100, 200, 500 or more times the serum concentration about one hour after ultrasonic dispersion of the composition. In some embodiments, the tissue concentration is about 1, 10, 20, 40, 50, 100, 200, 500 or more times the serum concentration about two hours after ultrasonic dispersion of the composition. In some embodiments the concentration of the composition in the serum at a given time following local dispersion by ultrasound is 1, 10, 50, 100, 1000 or more times less than the serum concentration that would be achieved by the same dose given systemically.

Antibiotic Administration

Figure 2:
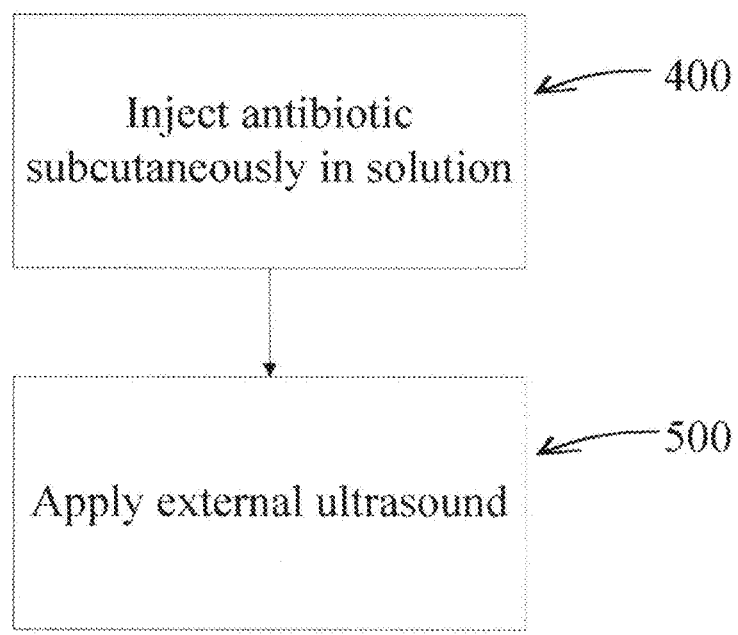
FIG. 2 is a flowchart illustrating a second embodiment.

A patient identified as suffering from or at risk of having a bacterial infection can be treated using the methods described herein, for example as illustrated in FIG. 2. An infected tissue in the patient is identified as a target tissue, where an antibiotic is to be delivered. One or more antibiotics are delivered to the target tissue 400 or in the vicinity of the target tissue. For example, a solution comprising the antibiotic can be delivered superficially or subcutaneously into or adjacent to the infected tissue by injection or infusion. The volume of solution and amount of antibiotic in the solution can be selected by the skilled practitioner based on the particular circumstances. In some embodiments the antibiotic may be provided in 100 cc of solution, such as saline or an isotonic solution. In some embodiments the antibiotic may be provided in 250 cc of solution. In some embodiments from 1 to about 5 g of antibiotic is delivered.

A delivery fluid is provided to the area where the antibiotic is delivered, for example as described above. The delivery fluid may be provided with the antibiotic. For example, the antibiotic may be dissolved in the delivery fluid or in suspension in the delivery fluid. However, in some embodiments a delivery fluid may be provided before the antibiotic or after the antibiotic. In some embodiments the antibiotic is in solution in the delivery fluid. In some embodiments the antibiotic is delivered in solution and additional delivery fluid is provided separately.

Subsequent to provision of the antibiotic and the delivery fluid, transcutaneous ultrasound is applied to disperse the antibiotic 500, such that an effective concentration is obtained in the target tissue. Delivery of ultrasound can be as described above. In some embodiments the ultrasound is provided at a frequency of about 1 to 3.3 MHz and a power of about 1 to 3 watts/cm$^2$.

The clinical efficacy of the treatment can be assessed and one or more aspects of the process adjusted to increase efficacy in subsequent rounds of therapy, if necessary. For example, one or more of the type of antibiotic, dosage, delivery location, amount and type of delivery fluid, power of ultrasound, duration of ultrasound and location of ultrasound can be adjusted to increase the therapeutic efficacy. The process can be repeated, one, two, three, four, five or more times to achieve the desired clinical endpoints. In some embodiments, a single treatment is necessary to resolve the infection.

The infection may be associated with any type of bacteria. In some embodiments, for example, the bacterial infection may be methicillin resistant *Staphylococcus aureus* (MRSA). In some embodiments, the infection may be, for example and without limitation, *Pseudomonas*, Beta Hemolytic Strep, or *Propionibacterium acnes*.

Any type of bacterial tissue infection may be treated. In some embodiments, the infection may include but is not limited to cellulitis, abscesses, furuncles, and carbuncles.

The antibiotic is not limited in any way and may be selected by the practitioner based on the specific circumstances, such as the type of infection present, for example causal bacteria by culture, tissue type, patient allergies, etc..... In some embodiments, at least one of the antibiotics is Cefazolin. In some embodiments at least one of the antibiotics is Vancomycin. In some embodiments, at least one of the antibiotics is a cephalosporin antibiotic, such as, 7-ACA, Carbacephem, Cefacetrile, Cefaclor, Cefadroxil, Cefalexin, Cefaloglycin, Cefalonium, Cefalotin, Cefamandole, Cefapirin, Cefatrizine, Cefazaflur, Cefazedone, Cefazolin, Cefbuperazone, Cefcapene, Cefclidine, Cefdaloxime, Cefdinir, Cefditoren, Cefepime, Cefetamet, Cefixime, Cefluprenam, Cefmatilen, Cefmenoxime, Cefmetazole, Cefminox, Cefodizime, Cefonicid, Cefoperazone, Coforanide, Cefoselis, Cefotaxime, Cefotetan, Cefotiam, Cefovecin, Cefoxitin, Cefozopran, Cefpimizole, Cefpiramide, Cefpirome, Cefpodoxime, Cefprozil, Cefquinome, Cefradine, Cefroxadine, Cefsulodin, Ceftaroline fosamil, Ceftazidime, Cefteram, Ceftezole, Ceftibuten, Ceftiofur, Ceftiolene, Ceftizoxime, Ceftobiprole, Ceftriaxone, Cefuroxime, Cefuzonam, Cephaloridine, Cephalosporin C, Cephamycin, Flomoxef, Latamoxef, and Loracarbef. In some embodiments, at least one of the antibiotics is Cipro and/or clinimycin. In some embodiments the antibiotic comprises a beta.-lactam antibiotic.

As discussed above, in some embodiments, the antibiotic may be provided in solution. For example, suitable isotonic solutions for dissolving an antibiotic agent may be used for infusion or injection, for example, saline or ringer's lactate, with the optional addition of epinephrine or xylocaine.

As discussed above, the dosage to be administered may be determined based on the particular circumstances, such as the type or degree of infection, whether the antibiotic is used to treat an existing infection or as a prophylactic, the tissue type, and the power of the ultrasound to be used.

In some embodiments the antibiotic is injected or infused subcutaneously into or in the vicinity of the infected tissue. In some embodiments the antibiotic is injected subcutaneously over the infected tissue. In some embodiments the antibiotic is injected at a distance 1, 2, 3, 4, 5, 6, 7, 8, 9, 10 or more centimeters from the infected tissue.

As discussed above, following provision of the antibiotic and the delivery fluid, ultrasound is applied to the area to disperse the antibiotic in the infected tissue. The frequency of ultrasound delivered to the target tissue can be selected as desired for a given situation. For example, the ultrasound may be delivered at a frequency of about 0.5 to about 10 MHz, about 1 to about 5 MHz or about 1 to about 3.3 MHz. In some embodiments, the ultrasonic field is introduced into the tissue through the skin at a frequency of about 1 MHz.

In some embodiments, high power ultrasound is used to disperse the antibiotic in the target tissue. For example, the ultrasound may be applied at a power of 0.1 to 25 watts/cm$^2$, about 1 to 10 watts/cm$^2$, or about 1 to 3 watts/cm$^2$. Preferably, the ultrasound is applied at a power that does not result in a burn to the tissue. In some embodiments, the ultrasound is applied at a power of up to about 3 watts/cm$^2$. The power can be controlled to achieve the desired concentration in a target tissue, taking into account such factors as tissue density, distance of the target tissue from the site of administration of the antibiotic and the size of the target tissue.

In some embodiments, the dispersed drug is present in the target tissue at a high concentration. Concentration in the target tissue can be measured, and the procedure adjusted if necessary to increase (or decrease) the concentration.

In some embodiments the initial concentration in the target tissue following ultrasonic dispersal of the antibiotic is at least about 100, 200, 300, 400, 500, 600, 700, 800, 900 or 1,000 µg/ml or greater. In some embodiments the maximum concentration achieved in the target tissue after ultrasonic dispersion may be from about 1 to about 10000 µg/ml, 1 to about 5000 micrograms/ml, or 1 to about 2000 micrograms/ml. In some embodiments the maximum concentration achieved in the target tissue after ultrasonic dispersion may be from about 500 to about 10000 µg/ml, 500 to about 5000 micrograms/ml, or 500 to about 2000 micrograms/ml. In some embodiments the initial concentration of antibiotic in the target tissue following ultrasonic dispersal is about 500 to about 10,000 µg/ml or more, about 500 to about 5000 µg/ml or more, or about 500 to about 1,000 µg/ml or more. In some embodiments the initial concentration of antibiotic in the target tissue after ultrasonic dispersion is about 2000 micrograms/ml or greater. In some embodiments, the target tissue concentration is about 4,500 µg/ml following the injection and dispersion of one gram of Cefazolin in 100 ml of saline.

In some embodiments an effective concentration of antibiotic is obtained as far as 7 or more centimeters from the site where the antibiotic is injected or otherwise provided.

In some embodiments, the dispersed antibiotic may be present in the target tissue at high concentrations for an extended period of time (e.g. 1, 2 or more hours after administration). In some embodiments, the concentration of antibiotic may be about 1000 micrograms/ml or more about one hour after provision, for example by subcutaneous injection, and ultrasonic dispersal. In some embodiments, the concentration may be about 2000 micrograms/ml or more about one hour after provision, such as by subcutaneous injection, and ultrasonic dispersal. In some embodiments, the concentration may be about 800 micrograms/ml or more about two hours after provision, such as by subcutaneous injection, and ultrasonic dispersal.

In some embodiments, the dispersed antibiotic may be present in the target tissue at high concentrations, but present at low systemic concentrations. In some embodiments, the tissue concentration in the target tissue is about 10, 25, 50, 100, 200, 400, 500, 1000 or more times the serum concentration immediately after ultrasonic dispersion of the drug. For example, in some experiments, tissue concentration was about 2216.47 ug/ml and serum concentration was about 5.16 ug/ml just after ultrasonic dispersion of the drug. In some embodiments, the tissue concentration in the target tissue is about 1, 10, 20, 40, 50, 75, 100, 200 or more times the serum concentration about one hour after ultrasonic dispersion of the antibiotic. For example, in some experiments, the tissue concentration was about 1142.78 ug/ml and serum concentration was about 28.72 ug/ml about 1 hour after ultrasonic dispersion of the antibiotic. In some embodiments, the tissue concentration is about 1, 10, 20, 40, 50 or more times the serum concentration about two hours after ultrasonic dispersion of the drug. For example, in some experiments, tissue concentration was about 814.37 ug/ml and serum concentration was about 20.61 ug/ml about two hours after dispersion of the drug.

In some embodiments, the antibiotic may be present in the target tissue at a concentration higher than a concentration resulting from another method that does not use ultrasonic dispersal, for example, delivery by mouth, injection into a muscle or intravenous injection or infusion. For example, in some embodiments, an antibiotic can be delivered directly to an infected tissue at a 1000× greater maximum concentration than the maximum concentration that can be given by another method.

Table 1, below, illustrates the concentration of Cefazolin detected in the serum and a target tissue after administration by intravenous injection (IV) and after delivery and ultrasonic dispersal using the described methods.

TABLE 1

Concentrations of Cefalozin (expressed in µg/ml.)

| | Method | Serum | Serum 1 hr | Serum 2 hr | Tissue | Tissue 1 hr | Tissue 2 hrs |
|---|---|---|---|---|---|---|---|
| 1 | IV | 206.04 | 85.63 | | 4.57 | 3.38 | |
| 2 | IV | 192.29 | 86.53 | | before IV | 3.29 | |
| Average | IV | 199.48 | 86.08 | | 4.57 | 3.34 | |
| 1 | TPS | Sample lost | Sample lost | | 1361.15 | 448.88 | |
| 2 | TPS | 0.66 | 19.73 | | 1358.58 | 124.53 | |
| 3 | TPS | 15.75 | 26.77 | | 936.92 | 183.1 | |
| 4 | TPS | 9.94 | 22.89 | | 1666.71 | 1231.15 | |
| 5 | TPS | 9.92 | 14.53 | | 987.57 | 45.24 | |
| 6 | TPS | BDL | 11.14 | | 803.7 | 480.5 | 197.35 |
| 7 | TPS | 5.16 | 28.72 | 20.61 | 2216.47 | 1142.78 | 814.37 |
| Average | TPS | 8.29 | 20.63 | 20.61 | 1333.01 | 522.31 | 505.86 |

In some embodiments, the procedure can be used to disperse an antibiotic in a target tissue prior to surgery in order to help prevent infection. Thus, in some embodiments a surgical procedure may commence upon completion of the transcutaneous broadcast of ultrasonic energy to disperse an injected or infused antibiotic into a target tissue that may be susceptible to infection following surgery.

Delivery of Compositions to Treat Inflammation

In some embodiments the methods disclosed herein can be used to treat inflammation. In some embodiments, treatment of inflammation in areas not traditionally thought to be treatable by injection of a therapeutic agent may be possible. For example, injecting anti-inflammatory drugs directly into the joint space does not typically provide significant benefit because there is no blood supply within the joint. The methods disclosed herein allow for delivery of anti-inflammatory agents in such situations.

An anti-inflammatory agent, such as a steroid or NSAID is provided in the vicinity of a target tissue, such as by injection or infusion. A delivery fluid is provided. In some embodiments the anti-inflammatory is provided in the delivery fluid. For example, an anti-inflammatory agent may be dissolved in, or in suspension in, a delivery liquid that is injected or infused in the vicinity of the target tissue. External ultrasound is applied, essentially as described above, to disperse the anti-inflammatory in the target tissue. The process can be repeated as desired to control the inflammation. In some embodiments, an anti-inflammatory drug in solution is injected directly into the joint space and external ultrasound is applied to diffuse the drug into the inflamed tissue.

In some embodiments the inflammatory condition may be, for example, arthritis, rheumatoid arthritis, lupus, Sjögren's syndrome, or gout.

In some embodiments a steroid or other anti-inflammatory is used to treat arthritis. The anti-inflammatory is injected and directly into the joint capsule or bursa (lubricating sac between certain tendons and the bones beneath them) or around tendons and other soft tissue areas and ultrasonically dispersed into the inflamed tissue by the methods described herein. For example, the anti-inflammatory may be delivered by subcutaneous injection and dispersed into the inflamed tissue by external ultrasonic dispersion as described herein.

Much higher concentrations of anti-inflammatory medication can thus be delivered directly to the desired area without the side effects of large doses given systemically.

Delivery of Therapeutic Agents to Treat Cancer

In some embodiments the methods disclosed herein can be used to deliver cancer therapeutics to cancerous tissue in a patient identified as in need of such treatment.

An anti-cancer agent, such as a chemotherapeutic agent, is provided in the vicinity of a target tissue, such as by injection. The anti-cancer agent can be selected by the skilled practitioner based on the particular circumstances, including, for example, the type of cancer and the type of tissue to be treated. The target tissue may be, for example, a tumor. A delivery fluid is provided. In some embodiments the anti-cancer agent is provided in the delivery fluid. For example, an anti-cancer agent may be dissolved in, or in suspension in, a delivery liquid that is injected or infused in the vicinity of the cancerous tissue. The mount of delivery fluid as well as the concentration of the therapeutic composition can also be selected based on the particular circumstances. External ultrasound is applied, essentially as described above, to disperse the anti-cancer agent in the target cancerous tissue. The process can be repeated as desired.

Because systemic administration is not used and the anti-cancer agent is delivered locally to the cancerous tissue, higher concentration of the anti-cancer agent can be used than could be used by other delivery methods. Further, because delivery is not dependent on blood supply, cancers that are difficult to treat because they are located in an area with limited or decreased blood supply may be treated more effectively using the disclosed methods. For example, chest wall recurrence of breast cancer is very difficult to treat because of the decreased blood supply caused by radiation therapy. The methods described herein can be used to deliver an adequate concentration of a chemotherapeutic agent directly into the tumor independent of blood supply. This greatly reduces the severe side effects of giving chemotherapy intravenously while delivering an effective dose.

Other Therapeutics/Diagnostics

The present methods can be used in any situation in which a composition is to be delivered to a tissue, particularly where delivery by traditional methods is limited by the lack of adequate blood supply. In some embodiments the composition is a pharmaceutical. For example, in some embodiments, a composition that may be delivered by the methods disclosed herein may include, but is not limited to a pharmaceutical for treating an infection or infestation. Some non-limiting examples include antibiotics, antifungals, antileprotics, antituberculous drugs, antimalarials, anthelmintics, amoebicides, antivirals, and antiprotozoals. In some embodiments, the composition may comprise a pharmaceutical for treatment of a disease or disorder of the immune system or that acts through or is a component of the immune system. For example, vaccines, immunoglobulins, immunosuppressants, interferons, and monoclonal antibodies. In some embodiments, the composition comprises a corticosteroid or steroid. For example, in some embodiments, the steroid comprises Triamcinolone (e.g. Kenalog). Other pharmaceuticals that can be delivered by the disclosed methods will be apparent to the skilled artisan.

While described herein primarily in terms of delivery of therapeutic agents to a target tissue, in some embodiments other types of compositions may be delivered. For example, diagnostic compositions can be delivered to a tissue. Diagnostic compositions may be, for example, small molecules, peptides, antibodies or other proteins that allow for the detection of particular pathogens, cell types, or other indicia of a disease or disorder. In some embodiments, for example, a diagnostic reagent may be ultrasonically dispersed in a tissue to determine whether or not a particular target is present in the tissue. For example, a diagnostic reagent that is selective for a cancer target may be used to identify the presence of cancerous cells in a particular tissue. In other embodiments a diagnostic may be ultrasonically dispersed in a tissue to identify the presence of a particular pathogen in a tissue.

The following examples are offered for illustrative purposes only, and are not intended to limit the scope of the claims in any way. Indeed, various modifications in addition to those shown and described herein will become apparent to those skilled in the art from the foregoing description and fall within the scope of the appended claims.

EXAMPLES

Example 1: Delivery of a Therapeutic Agent to a Target Tissue

A target tissue is identified in a patient where delivery of a therapeutic agent is desired.

A solution of the therapeutic agent is prepared and delivered in a superficial subcutaneous plane into and/or adjacent to the target tissue. Delivery may be, for example, with a needle and syringe or through an infusion cannula.

An ultrasound device is utilized, such as the Silberg Tissue Preparation Systems™ Model ME 800 (9801427), available from Mettler Surgical (Anaheim, Calif.). Power output of the device is set to about 3 watts/cm². The ultrasonic applicator is covered with a sterile ultrasound shield with ultrasonic gel placed on the applicator inside the shield. Water-soluble sterile gel is placed on the patient's skin over the target tissue prior to use of the ultrasound. The countdown timer, if present, is set to approximately 1-3 minutes depending upon the amount and depth of tissue to be treated.

The applicator is placed in contact with the patient and ultrasonic power is applied to the skin overlying the target tissue. The applicator is moved slowly at all times while the power is engaged. The therapeutic agent is thereby dispersed in the target tissue.

Efficacy of the treatment is assessed at an appropriate period following the procedure. If necessary or desirable, the treatment may be repeated one or more additional times.

Example 2: Direct Antibiotic Delivery of Cefazolin to a Target Tissue Treat MRSA A patient is identified suffering from an MRSA tissue infection. One gram of Cefazolin is dissolved in 100 ml saline for injection. The Cefazolin is injected in a superficial subcutaneous plane into or adjacent to the infected tissue by use of a needle and syringe or with an infusion cannula.

An ultrasound device is utilized, such as the Silberg Tissue Preparation Systems™ Model ME 800 (9801427), available from Mettler Surgical (Anaheim, Calif.). Power output of the device is set to 3 watts/cm². The ultrasonic applicator is covered with a sterile ultrasound shield with ultrasonic gel placed on the applicator inside the shield. Water-soluble sterile gel is placed on the skin of the patient prior to use of the ultrasound.

The countdown timer is set to 1-3 minutes depending upon the amount and depth of tissue to be treated.

The applicator is placed in contact with the infected tissue and the ultrasonic power is applied. The applicator is moved slowly over the target tissue and remains in contact with the tissue while the power is engaged.

Efficacy of the treatment is assessed at an appropriate time following the procedure, and the procedure is repeated as necessary.

Example 3: Cefazolin to Treat MRSA Cellulitis

A prophylactic does of the antibiotic Cafazolin was delivered to a patient by the above procedure prior to elective abdominoplasty using the Silberg Tissue Preparation Systems™ Model ME 800 (9801427) Mettler Surgical, Anaheim, Calif.). About 250 cc of prewarmed saline containing 1 gm of Cefazolin was injected under a surgical incision line that was about 5 cm long. Small samples of adipose tissue were taken during the surgical procedure to determine the Cefazolin concentration throughout the procedure. Further, blood serum samples were taken during the procedure and the Cefazolin concentration was determined.

Figure 3:
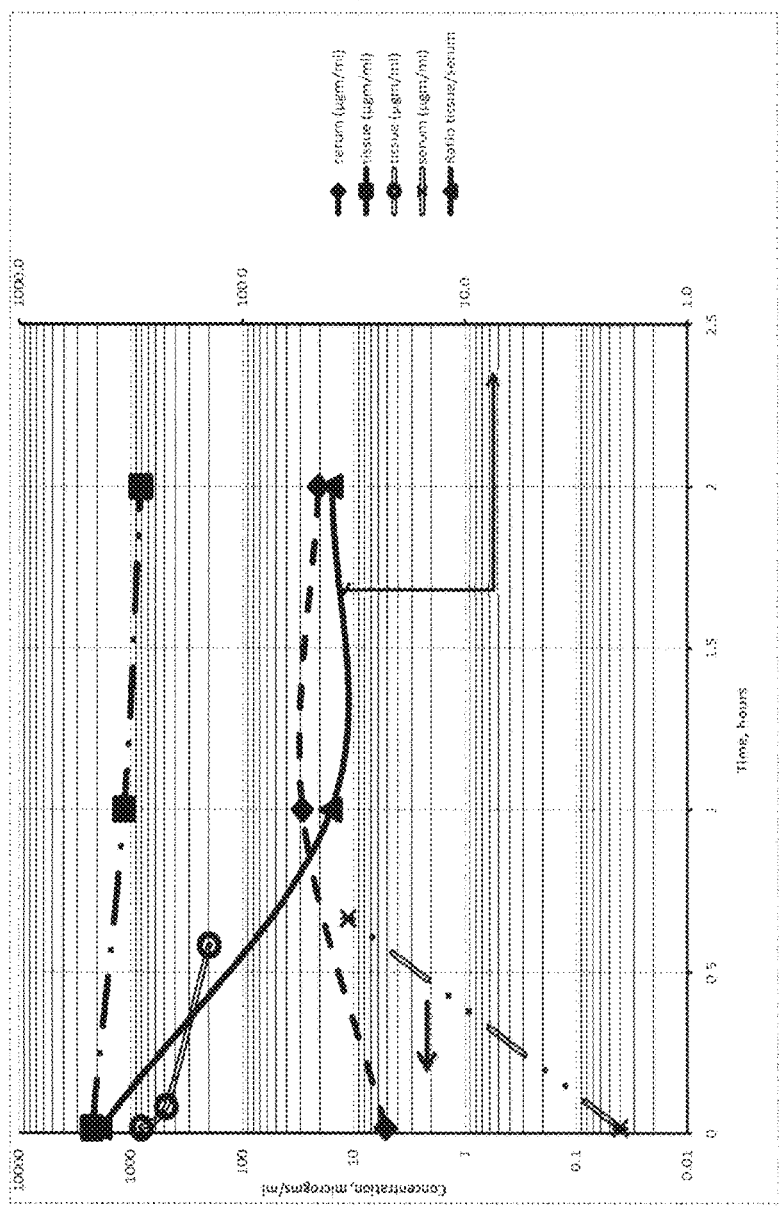
FIG. 3 is a graph showing adipose tissue and blood serum concentrations of Cefazolin over time.

As illustrated in FIG. 3, which plots the concentration of Cefazolin over time, adipose tissue concentration of Cefazolin at the start of surgery, for the total dose of 1 gram were higher than those seen when the Cefazolin is injected systemically (Ohge et al. Jpn J Surg (1999) 29:1233-1236). The Cefazolin concentration in the adipose tissue was about 800 .mu.g/ml at the beginning of surgery and dropped to about 200 .mu.g/ml about 50 minutes later, achieving about a 50 times greater concentration than was achieved by the intravenous administration reported in Ohge et al.

Further, FIG. 3 also indicates that the blood serum concentrations of Cefazolin increased to about 10 .mu.g/ml when surgery was completed about an hour later.

Notably, the above method yields antibiotic concentrations in tissue that are far beyond what could be achieved by IV delivery.

Example 4: Cefazolin to Treat MRSA Cellulitis

A recent IRB study done under IND number 75,736 demonstrated a subcutaneous tissue concentration of Cefazolin in deep subcutaneous adipose of the abdomen reaching 2000 micrograms/ml in one hour and 800 micrograms/ml in two hours after subcutaneous injection of Cefazolin at a concentration of one gram in 250 ml of saline followed by dispersion using external high frequency ultrasound for three minutes. This compared with tissue levels of 3-5 micrograms/ml of Cefazolin after one hour when given intravenously.

Sensitivity of a given bacterium to an antibiotic is measured in vitro using an MIC that is obtainable by standard methods. In a study by David Nicolau at the Hartford Center for Anti-Infective Research and Development, the highest MIC for Cefazolin against MRSA in vitro was 512 micrograms/ml. The concentration obtained using direct antibiotic delivery with dispersal by ultrasound far exceeded this MIC.

Example 5: Cefazolin to Treat MRSA Cellulitis

A 79 year old man with an MRSA rash who required an urgent coronary artery bypass was treated. Cefazolin at a concentration of one gram in 100 cc's of saline was infused subcutaneously over the sternum followed by one minute of ultrasound at 3 watts/cm$^2$. He healed without complication and the surrounding rash cleared.

Example 6: Cefazolin to Treat MRSA Infection

A 58 year old woman with multiple sclerosis was admitted with an infected stage 4 ischial pressure ulcer. Cultures from the ulcer grew MRSA. Cefazolin was injected and dispersed using ultrasound at 3 watts/cm$^2$ for 3 minutes. This was followed by V.A.C. dressing for 2 days. The local inflammation was gone when the V.A.C. was removed. A rotation flap closure was done that healed without complication. Cultures from the drain were negative. She was discharged after one week and on follow-up there was no recurrence of the infection or wound breakdown.

Example 7: Cefazolin to Treat *Pseudomonas* Infection

Figure 5A:
FIGS. 5A and 5B are photographs showing infected tissue of a patient prior to treatment.
Figure 5B:
Figure 5C:
FIG. 5C is a photograph showing the infected tissue after treatment in accordance with embodiments of the methods disclosed herein.

A 48 year old diabetic man with massive necrotizing MRSA infection of his leg underwent debridement by the general surgeon. One gram of Ceftazidme in 100 cc saline was injected and dispersed in the infected tissue using ultrasound. Ultrasound was applied at 3 watts/cm$^2$. This was followed by a V.A.C. dressing for two days. After this time the V.A.C. was removed and the open areas were grafted with a mesh graft that took 100%. See FIGS. 5A-C.

Example 8: Treatment of Fournier's Gangrene

A 46 year old man weighing 450 pounds was admitted with Fournier's gangrene involving the left groin and left side of his scrotum. The wound had been debrided by the urologist but still had grossly indurated surrounding soft tissue. The entire wound together with the surrounding indurated tissues was treated by injecting Cefazolin in solution followed by high power ultrasound. The wound was closed primarily and healed without complication. He was discharged in 7 days after treatment.

Example 9: Treatment of Cellulitis

A 9 year old girl developed sudden onset of a left groin cellulitis with extreme pain. The methods disclosed herein were used to deliver and disperse one gram of Cefaolin in 100 cc saline. The drug was dispersed using ultrasound at 3 watts/cm2 for two minutes. The next day she was pain free and the area of induration was ½ the size.

Example 10: Treatment of MRSA Cellulitis

Figure 6A:
FIG. 6A is a photograph showing infected tissue of a patient prior to treatment.
Figure 6B:
FIG. 6B is a photograph showing the infected tissue after treatment in accordance with embodiments of the methods disclosed herein.

A 73 year old diabetic woman who had been a smoker for most of her life developed an MRSA cellulitis of the pre-tibia including osteomyelitis from a minor trauma. The infection was treated with triple intravenous antibiotics. There was no response to the intravenous antibiotics. One gram of Cefazolin in 100 cc saline was injected and dispersed using high power ultrasound at 3 watts/cm2 for three minutes. Pain decreased rapidly and the soft tissue and bone infection healed. See FIG. 6A-B.

Example 11: Treatment of Beta Hemolytic Strep Infection

A 42 year old man with rapidly progressing beta hemolytic strep infection of his mid tibial region was treated by administering antibiotic and dispersing the antibiotic in the infected tissue using high power ultrasound. Evidence of infection was gone after 48 hours and the missing skin was grafted.

Example 12: Delivery of an Anti-Inflammatory Agent to a Target Tissue

An inflamed tissue is identified in a patient. A solution of an anti-inflammatory agent, such as a steroid or NSAID, is prepared and delivered into and/or adjacent to the inflamed tissue. For example, the solution may be delivered into a joint capsule. Delivery may be, for example, with a needle and syringe or through an infusion cannula.

An ultrasound device is utilized, such as the Silberg Tissue Preparation Systems™ Model ME 800 (9801427), available from Mettler Surgical (Anaheim, Calif.). Power output of the device is set to about 3 watts/cm$^2$. The ultrasonic applicator is covered with a sterile ultrasound shield with ultrasonic gel placed on the applicator inside the shield. Water-soluble sterile gel is placed on the patient's skin over the target tissue prior to use of the ultrasound. The countdown timer, if present, is set to approximately 1-3 minutes depending upon the amount and depth of tissue to be treated.

The applicator is placed in contact with the patient and ultrasonic power is applied to the skin overlying the inflamed tissue. The applicator is moved slowly at all times while the power is engaged. The anti-inflammatory agent is thereby dispersed in the inflamed tissue.

Efficacy of the treatment is assessed at an appropriate period following the procedure. If necessary or desirable, the treatment may be repeated one or more additional times.

Example 13: Delivery of an Anti-Cancer Agent to a Target Tissue

An cancerous tissue is identified in a patient. A solution of an anti-cancer agent is prepared and delivered into and/or adjacent to the cancerous tissue. Delivery may be, for example, with a needle and syringe or through an infusion cannula.

An ultrasound device is utilized, such as the Silberg Tissue Preparation Systems™ Model ME 800 (9801427), available from Mettler Surgical (Anaheim, Calif.). Power output of the device is set to about 3 watts/cm$^2$. The ultrasonic applicator is covered with a sterile ultrasound shield with ultrasonic gel placed on the applicator inside the shield. Water-soluble sterile gel is placed on the patient's skin over the target tissue prior to use of the ultrasound. The countdown timer, if present, is set to approximately 1-3 minutes depending upon the amount and depth of tissue to be treated.

The applicator is placed in contact with the patient and ultrasonic power is applied to the skin overlying the cancerous tissue. The applicator is moved slowly at all times while the power is engaged. The anti-inflammatory agent is thereby dispersed in the cancerous tissue.

Efficacy of the treatment is assessed at an appropriate period following the procedure. If necessary or desirable, the treatment may be repeated one or more additional times.

What is claimed is:

1. A method of treating an infection comprising:
identifying a treatment field associated with the infection;
subcutaneously injecting a solution comprising a therapeutic dose of a drug dissolved therein to the treatment field and in a vicinity of the infected tissue, wherein the infection comprises a methicillin resistant *staphylococcus aureus* infection with a minimum inhibitory concentration of at least 64 micrograms/ml with respect to Cefazolin and wherein the drug comprises Cefazolin; and
applying ultrasound transcutaneously toward the treatment field associated with the infected tissue and the subcutaneously injected solution, wherein the transcutaneously applied ultrasound is applied for 5 minutes or less at a power density of 2.5 to 4 W/cm2 and at a frequency of less than 5 MHz such that the ultrasound interacts with the subcutaneously injected solution to disperse the solution with the therapeutic dose of drug dissolved therein through the treatment field and into the infected tissue via microstreaming or by cavitation, the therapeutic dose of drug dissolved in the solution being dispersed through the infected tissue at therapeutically effective concentrations for treating the infection; and wherein the concentration of drug in the infected tissue is therapeutically effective against the infection while maintaining serum concentration of the drug to less than 10 micrograms/ml one hour after the application of transcutaneous ultrasound; and
monitoring a temperature during application of the transcutaneous ultrasound with a temperature monitor to identify a need to cease the broadcast of ultrasound toward the treatment field when a monitored temperature exceeds a temperature threshold.

2. The infection treatment method of claim 1, further comprising:
prewarming the solution with a solution warmer prior to subcutaneous injection of the solution;
applying a sterile sheath to an ultrasonic transducer head of an ultrasound system to protect a skin of the patient from the ultrasonic transducer; and
wherein the solution is subcutaneously injected with an irrigating needle having a blunt tip for delivery of the solution with the therapeutic dose of drug dissolved therein into the treatment field.

3. The infection treatment method of claim 1, wherein 100 cc of the solution with the therapeutic dose of drug dissolved therein is injected subcutaneously, wherein the therapeutic dose of the drug dissolved in the at least 100 cc of solution is less than a therapeutic dose of the drug required for intravenous injection or for oral administration, and wherein a minimum inhibitory concentration of the drug with respect to the infection is more than ten times a drug concentration achievable by intravenous administration.

4. The infection treatment method of claim 1, wherein the infection comprises a *propionibacterium acnes* infection.

5. The infection treatment method of claim 1, wherein the infection comprises a cellulitis infection.

6. The infection treatment method of claim 1, wherein the infection comprises a furuncle.

7. The infection treatment method of claim 1, wherein the infection comprises a carbuncle.

8. The infection treatment method of claim 1, wherein the infection comprises a osteomyelitis.

9. A method of treating an infection comprising:
identifying a treatment field associated with the infection;
subcutaneously injecting a solution comprising a therapeutic dose of a drug dissolved therein to the treatment field and in a vicinity of the infected tissue, wherein the infection comprises a methicillin resistant *staphylococcus aureus* infection and wherein the solution includes a reduced therapeutic dose of Vancomycin dissolved therein, the reduced therapeutic dose of Vancomycin being less than an intravenous therapeutic dose of Vancomycin;
applying ultrasound transcutaneously toward the treatment field associated with the infected tissue and the subcutaneously injected solution, wherein the transcutaneously applied ultrasound is applied for 5 minutes or less at a power density of 2.5 to 4 W/cm2 and at a frequency of less than 5 MHz such that the ultrasound interacts with the subcutaneously injected solution to disperse the solution with the therapeutic dose of drug dissolved therein through the treatment field and into the infected tissue via microstreaming or by cavitation, the therapeutic dose of drug dissolved in the solution being dispersed through the infected tissue at therapeutically effective concentrations for treating the infection; and wherein the concentration of drug in the infected tissue is therapeutically effective against the infection while maintaining serum concentration of the drug to less than 10 micrograms/ml one hour after the application of transcutaneous ultrasound; and
monitoring a temperature during application of the transcutaneous ultrasound with a temperature monitor to identify a need to cease the broadcast of ultrasound toward the treatment field when a monitored temperature exceeds a temperature threshold.

10. The infection treatment method of claim 9, further comprising:
prewarming the solution with a solution warmer prior to subcutaneous injection of the solution;
applying a sterile sheath to an ultrasonic transducer head of an ultrasound system to protect a skin of the patient from the ultrasonic transducer; and wherein the solution is subcutaneously injected with an irrigating needle having a blunt tip for delivery of the solution with the therapeutic dose of drug dissolved therein into the treatment field.

11. The infection treatment method of claim 9, wherein 100 cc of the solution with the therapeutic dose of drug dissolved therein is injected subcutaneously, wherein the therapeutic dose of the drug dissolved in the at least 100 cc of solution is less than a therapeutic dose of the drug required for intravenous injection or for oral administration, and wherein a minimum inhibitory concentration of the drug with respect to the infection is more than ten times a drug concentration achievable by intravenous administration.

12. The infection treatment method of claim 9, wherein the infection comprises a *propionibacterium acnes* infection.

13. The infection treatment method of claim 9, wherein the infection comprises a cellulitis infection.

14. The infection treatment method of claim 9, wherein the infection comprises a furuncle.

15. The infection treatment method of claim 9, wherein the infection comprises a carbuncle.

16. The infection treatment method of claim 9, wherein the infection comprises a osteomyelitis.

* * * * *